United States Patent
Glassy et al.

(12)

(10) Patent No.: US 6,355,444 B1
(45) Date of Patent: *Mar. 12, 2002

(54) CARCINOMA ASSOCIATED ANTIGEN (SK1) MONOCLONAL ANTIBODIES AGAINST SK1, METHODS OF PRODUCING THESE ANTIBODIES AND USES THEREFOR

(75) Inventors: Mark C. Glassy, San Diego, CA (US); Helena R. Chang, Providence, RI (US); Keiji Koda, Chiba (JP)

(73) Assignee: Viventia Biotech Inc., Toronto (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/872,399

(22) Filed: Jun. 10, 1997

Related U.S. Application Data

(60) Division of application No. 08/201,243, filed on Feb. 24, 1994, now Pat. No. 5,637,493, which is a continuation-in-part of application No. 07/827,717, filed on Jan. 29, 1992, now abandoned.

(51) Int. Cl.[7] .................... A61K 49/00; A61K 5/055; G01N 33/53; G01N 35/574
(52) U.S. Cl. .................. 435/7.23; 424/1.11; 424/1.49; 424/9.1; 424/9.3; 435/7.1; 435/7.2; 435/344.1; 530/388.15; 530/388.8; 530/388.85
(58) Field of Search .................. 435/327, 344.1, 435/7.2, 7.1, 7.23; 424/1.11, 1.49, 9.1, 9.3; 530/387.2, 388.85, 388.15, 388

(56) References Cited

U.S. PATENT DOCUMENTS

| 4,618,577 A | 10/1986 | Handley et al. |
| 4,761,377 A | 8/1988 | Glassy et al. |
| 5,024,946 A | 6/1991 | Abe et al. |
| 5,134,075 A | 7/1992 | Hellstrom et al. |

FOREIGN PATENT DOCUMENTS

| EP | 0141783 | 10/1984 |
| EP | 0285173 | 3/1988 |

OTHER PUBLICATIONS

Koda et al., Arch. Surg., 1990, 125:1591.
Chang et al., Cancer Res., 1993, 53:1122.
Proceedings Eighty–Third Annual Meeting of the American Association for Cancer Research, May 20–23, 1992, San Diego, CA, vol. 33, pp. 315, sections 1881 and 1877, Mar. 1992.
Koda et al., "Generation of Human Monoclonal Antibodies Against Colon Cancer", Archives of Surgery, vol. 125, no. 12, pp. 1591–1597, Dec. 1990.
Erb, Karin, Antigenes Recognized by Two Human Monoclonal 1gM anticolon . . . , Hum. Antibod., Hybridomas, 1991, vol. 2, Oct., pp. 215–221.

*Primary Examiner*—David Saunders
*Assistant Examiner*—Amy DeCloux
(74) *Attorney, Agent, or Firm*—Morrison & Foerster LLP

(57) ABSTRACT

Carcinoma associated antigen (SK1) and monoclonal antibodies and methods for detecting and ameliorating malignant disease. The monoclonal antibodies are specifically reactive with epitopes present on SK1.

6 Claims, 1 Drawing Sheet

Expression of AgSK1 in Human Cell Lines: NP-40 Extracts

CARCINOMA ASSOCIATED ANTIGEN (SK1) MONOCLONAL ANTIBODIES AGAINST SK1, METHODS OF PRODUCING THESE ANTIBODIES AND USES THEREFOR

This application is a divisional application of application U.S. Ser. No. 08/201,243, filed Feb. 24, 1994, and issued as U.S. Pat. No. 5,637,493 on Jun. 10, 1997, which is a continuation-in-part of application U.S. Ser. No. 07/827,717, filed Jan. 29, 1992, now abandoned.

BACKGROUND OF THE INVENTION

1. Field of the Invention

This invention relates to a novel carcinoma associated antigen (SK1) which is associated with various malignancies and monoclonal antibodies specific for epitopes on SK1.

2. Description of the Background Art

Murine monoclonal antibodies have been shown to mediate effective cytotoxicity to target cells in vitro; however, when utilized in vivo with humans, they have not achieved remarkable results. This is partially due to (i) the foreign nature of the injected murine proteins which leads to the development of a human anti-mouse antibody (HAMA) response, and (ii) the human effector functions which may not be fully activated by a murine antibody. In contrast, the dramatic effects which have been observed in systemically treating septic patients with purified human monoclonal or polyclonal antibodies (Ziegler, et al., *The New England J. Med*, 324:429–436, 1991; Kurtzberg, et al., *Am. J. Pediatr. Hematol. Oncol.*, 9:299–301, 1987) and by intralesional therapy of melanoma suggests that the clinical use of human monoclonal antibodies (HuMAbs) (Irie, et al., *Proc. Natl. Acad. Sci. USA*, 83:8694–8698, 1986) will be successful. Thus, the potential use of human Mabs for cancer therapy is attractive.

Recent progress in the field of HuMAb technology has made it possible to generate numerous hybridomas of various specificities. Combined with knowledge gained in the understanding of the human immune response to cancer antigens (Lloyd, et al., *Cancer Res.*, 49:3445–3451, 1989), several HuMAbs against tumor associated antigens (TAAs) have been produced and characterized. The reported tumor associated antigens recognized by HuMAbs include cell surface (Yoshikawa, et al., *Jpn. J. Cancer Res. (Gann)*, 80:546–553, 1989; Yamaguchi, et al., *Proc. Natl. Acad. Sci. USA*, 84:2416–2420; Haspel, et al., *Cancer Res.*, 45:3951–3961, 1985; Cote, et al., *Proc. Natl. Acad. Sci. USA*, 83:2959–2963, 1986; Glassy, *Cancer Res.*, 47:5181–5188, 1987; and Borup-Christensen, et al., *Cancer Detect. Prevent. Suppl.*, 1:207–215), cytoplasmic (Haspel, et al., *Cancer Res.*, 45:3951–3961, 1985; Cote, et al., *Proc. Natl. Acad. Sci. USA*, 83:2959–2963, 1986; Glassy, *Cancer Res.*, 47:5181–5188; Borup-Christensen, et al., *Cancer Detect Prevent Suppl.*, 1:207–215, 1987; Kan-Mitchell, et al., *Cancer Res.*, 49:4536–4541, 1989; and Yoshikawa, et al., *Jpn. J. Cancer Res.*, 77:1122–1133, 1986), and nuclear antigens (McKnight, et al., *Hum. Antibod. Hybridomas*, 1:125–129, 1990).

At present, methods of limited effectiveness exist for treatment of various malignancies. Those drugs which are administered generally have severe side effects associated with their use. Accordingly, there exists a significant need to identify and purify an antigen associated with malignant diseases and to produce monoclonal antibodies which bind to epitopes on this antigen. Further, these antibodies are suitable agents for the diagnosis and treatment of malignancies expressing the SK1 antigen.

SUMMARY OF THE INVENTION

One way to ameliorate malignancies would be to suppress cells which preferentially express an antigen associated with carcinoma. This suppression could be accomplished, for example, by active immunization using an antigen, or a derivative thereof, preferentially present in malignant cells or by passive immunization by providing antibody to the antigen.

In order to provide a means to ameliorate malignant disease the invention provides substantially purified antigen which is preferentially expressed by malignant cells and monoclonal antibodies which bind to epitopes on the antigen. These monoclonal antibodies, if desired, can be labeled for therapeutic or diagnostic use.

An object of the present invention is to provide a method of detecting the carcinoma associated antigen (SK1) preferentially expressed in various malignant cells and tissues using a detectably labeled monoclonal antibody which binds to SK1 and determining whether the detectably labeled monoclonal antibody has bound to SK1.

Another object of the present invention is to provide methods for the in vitro and in vivo diagnosis of malignancy using detectably labeled monoclonal antibodies which react with an epitope present on SK1.

Another object of the invention is to provide methods for ameliorating malignant disease in an animal using unlabeled or therapeutically labeled monoclonal antibodies which react with SK1.

Alternatively, the invention provides methods for ameliorating malignant disease in an animal by inducing an immune response to the malignancy by immunizing the animal with SK1.

The present invention thus relates to a method of detecting SK1 which comprises contacting a source suspected of containing SK1 with a diagnostically effective amount of detectably labeled monoclonal antibody, or fragment thereof, having the specificity of a monoclonal antibody of the invention and determining whether the antibody binds to the source.

The invention further relates to a method of suppressing malignant disease in an animal which comprises administering to the animal a therapeutically effective amount of a (1) monoclonal antibody, or fragment thereof, wherein the antibody has the specificity of a monoclonal antibody of the invention, or (2) SK1.

A major advantage in the therapeutic and diagnostic use of SK1 and mono-clonal antibodies which bind to epitopes of SK1 is that the SK1 antigen occurs at high frequency in malignant cells. Consequently, there is a much greater probability of binding occurring to a malignant cell than to a normal cell. As a result of this fact, it is possible to use concentrations of the monoclonal antibody of the invention which are clinically effective, but pose minimal or no risk to normal host cells.

DETAILED DESCRIPTION OF THE INVENTION

Figure 1:
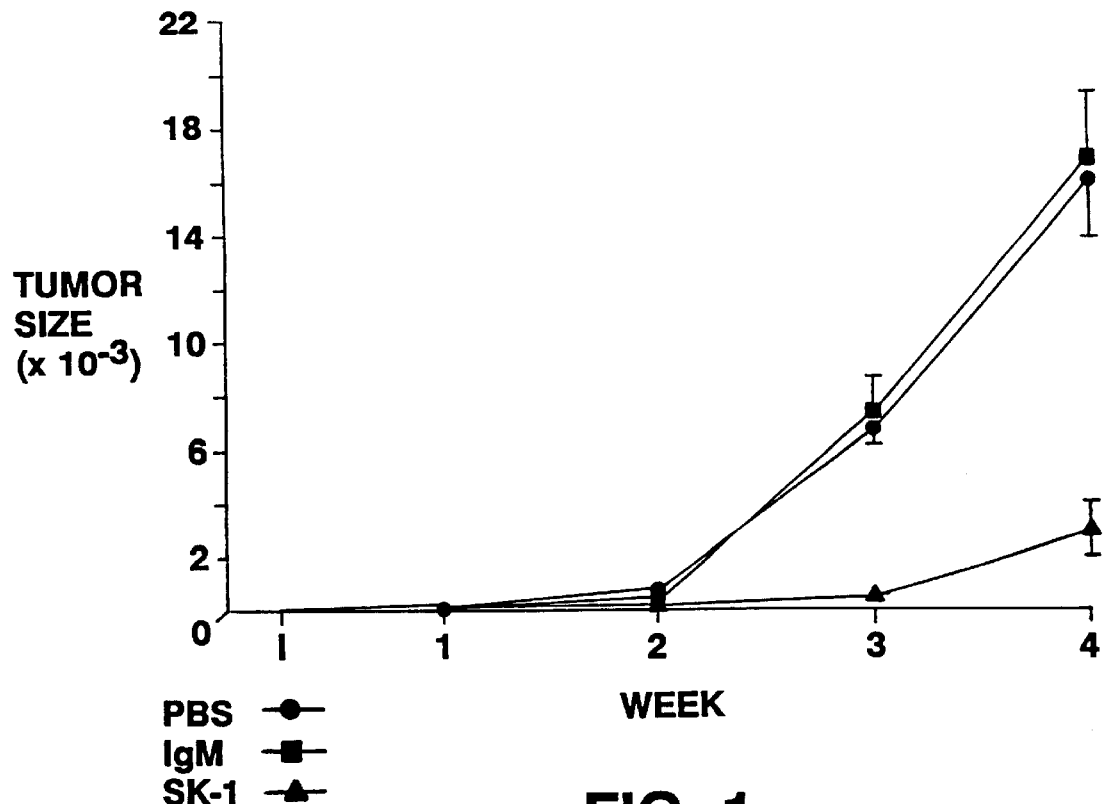
FIG. 1 shows tumor size versus time in an SK1 nude mouse xenograft model. (●=PBS control; ■=control IgM; and ▲=HuMAb to antigen SK1).

The present invention relates to a substantially purified antigen (SK1) which is preferentially expressed by malignant cells and to monoclonal antibodies with epitopic specificity for SK1. These monoclonal antibodies are highly useful for both the in vitro and in vivo immunological detection of antigens associated with these malignancies and for immunotherapy of cells bearing SK1.

In a preferred embodiment of the invention a monoclonal antibody is disclosed which binds to an epitope on SK1. This specificity enables the monoclonal antibody, and like monoclonal antibodies with like specificity, to be used to suppress growth of malignant cells having SK1. As a consequence, these monoclonal antibodies are useful in ameliorating malignant diseases such as colorectal carcinoma, gastric cancer, pancreatic cancer; and adenocarcinoma.

Methods of Producing and Characterizing Monoclonal Antibodies to SK1

The general method used for production of hybridomas secreting monoclonal antibodies is well known (Kohler and Milstein, *Nature*, 256:495, 1975). Briefly, lymph nodes from a patient with colon cancer were harvested from colectomy specimens and lymphocytes isolated. The lymphocytes were then immunized in vitro with carcinoembryonic antigen. Hybridomas were screened for production of antibody which bound to a colon cancer cell line.

In one aspect, the present invention is directed to monoclonal antibodies, and hybridomas which produce them, which are reactive with SK1. The isolation of hybridomas secreting monoclonal antibodies with the reactivity of the monoclonal antibodies of the invention can be accomplished using routine screening techniques to determine the elementary reaction pattern of the monoclonal antibody of interest. Thus, if a monoclonal antibody being tested binds with SK1, then the antibody being tested and the antibody produced by the hybridomas of the invention are equivalent.

Alternatively, since the invention teaches the substantial purification of the novel SK1 antigen, it is now possible to use this antigen for purposes of immunization to produce more hybridomas which secrete monoclonal antibodies specific for the SK1 antigen. This approach would have the added advantage of decreasing the repertoire of monoclonal antibodies generated by limiting the number of antigenic determinants presented at immunization. The monoclonal antibodies so produced could be screened for specificity for SK1 using standard techniques, for example, by binding SK1 to microtiter plate and measuring binding of the monoclonal antibody by an ELISA assay. The term "substantially pure form" when applied to SK1 means that SK1 is essentially free of other proteins with which SK1 is normally associated in nature.

It is also possible to evaluate, without undue experimentation, a monoclonal antibody to determine whether it has the same specificity as a monoclonal antibody of the invention by determining whether the monoclonal antibody being tested prevents a monoclonal antibody of the invention from binding 1) to the SK1 antigen, or 2) a malignant cell expressing the SK1 antigen with which the monoclonal antibody of the invention is normally reactive. If the monoclonal antibody being tested competes with the monoclonal antibody of the invention, as shown by a decrease in binding by the monoclonal antibody of the invention, then it is likely that the two monoclonal antibodies bind to the same, or a closely related, epitope.

Still another way to determine whether a monoclonal antibody has the specificity of a monoclonal antibody of the invention is to pre-incubate the monoclonal antibody of the invention with the SK1 antigen with which it is normally reactive, and determine if the monoclonal antibody being tested is inhibited in its ability to bind the antigen. If the monoclonal antibody being tested is inhibited then, in all likelihood, it has the same, or a closely related, epitopic specificity as the monoclonal antibody of the invention.

While the in vivo use of a monoclonal antibody from a foreign donor species in a different host recipient species is usually uncomplicated, a potential problem which may arise is the appearance of an adverse immunological response by the host to antigenic determinants present on the donor antibody. In some instances, this adverse response can be so severe as to curtail the in vivo use of the donor antibody in the host. Further, the adverse host response may serve to hinder the malignancy suppressing efficacy of the donor antibody. One way in which it is possible to circumvent the likelihood of an adverse immune response occurring in the host is by using chimeric antibodies (Sun, et al., *Hybridoma*, 5 (*Supplement* 1):S17, 1986; Oi, et al., *Bio Techniques*, 4(3: 214, 1986). Chimeric antibodies are antibodies in which the various domains of the antibodies' heavy and light chains are coded for by DNA from more than one species. Typically, a chimeric antibody will comprise the variable domains of the heavy ($V_H$) and light ($V_L$) chains derived from the donor species producing the antibody of desired antigenic specificity, and the constant domains of the heavy ($C_H$) and light ($C_L$) chains derived from the host recipient species. It is believed that by reducing the exposure of the host immune system to the antigenic determinants of the donor antibody domains, especially those in the $C_H$ region, the possibility of an adverse immunological response occurring in the recipient species will be reduced. Thus, for example, it is possible to produce a chimeric antibody for in vivo clinical use in humans which comprises mouse $V_H$ and $V_L$ domains coded for by DNA isolated from a hybridoma of the invention, such as ATCC HB 10905, and $C_H$ and $C_L$ domains coded for with DNA isolated from a human leukocyte.

Although the present invention encompasses all monoclonal antibodies which recognize the novel carcinoma antigen SK1, especially preferred are monoclonal antibodies of human origin. Such human monoclonal antibodies are exemplified by HuMAb(SK1) which is an IgM antibody produced by a hybridoma having accession number ATCC HB 10905.

Under certain circumstances, monoclonal antibodies of one isotype might be more preferable than those of another in terms of their diagnostic or therapeutic efficacy. For example, from studies on antibody-mediated cytolysis, it is known that unmodified mouse monoclonal antibodies of isotype gamma-2a and gamma-3 are generally more effective in lysing target cells than are antibodies of the gamma-1 isotype. This differential efficacy is thought to be due to the ability of the gamma-2a and gamma-3 isotypes to more actively participate in the cytolytic destruction of target cells. Particular isotypes of a monoclonal antibody can be prepared either directly, by selecting from the initial fusion, or prepared secondarily, from a parental hybridoma secreting a monoclonal antibody of different isotype by using the sib selection technique to isolate class-switch variants (Steplewski, et al., *Proceedings of the National Academy of Science, U.S.A.*, 82:8653, 1985; Spira, et al., *Journal of Immunological Methods*, 74:307, 1984). Thus, the monoclonal antibodies of the invention would include class-switch variants having specificity for an epitope on SK1.

The isolation of other hybridomas secreting monoclonal antibodies with the specificity of the monoclonal antibodies of the invention can also be accomplished by one of ordinary skill in the art by producing anti-idiotypic antibodies (Herlyn, et al., *Science*, 232:100, 1986). An anti-idiotypic antibody is an antibody which recognizes unique determinants present on the monoclonal antibody produced by the hybridoma of interest. These determinants are located in the hypervariable region of the antibody. It is this region which binds to a given epitope and, thus, it is responsible for the specificity of the antibody. The anti-idiotypic antibody can be prepared by immunizing an animal with the monoclonal antibody of interest. The animal immunized will recognize and respond to the idiotypic determinants of the immunizing antibody by producing an antibody to these idiotypic determinants. By using the anti-idiotypic antibodies of the second animal, which are specific for the monoclonal antibodies produced by a single hybridoma which was used to immunize the second animal, it is now possible to identify other clones with the same idiotype as the antibody of the hybridoma used for immunization.

Idiotypic identity between monoclonal antibodies of two hybridomas demonstrates that the two monoclonal antibodies are the same with respect to their recognition of the same epitopic determinant. Thus, by using antibodies to the epitopic determinants on a monoclonal antibody it is possible to identify other hybridomas expressing monoclonal antibodies of the same epitopic specificity.

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody. Thus, in this instance, the anti-idiotypic monoclonal antibody could be used for immunization since the anti-idiotype monoclonal antibody binding domain effectively acts as an antigen.

When the monoclonal antibodies of the invention are used in the form of fragments, such as, for example, Fab and F(ab')$_2$, and especially when these fragments are therapeutically labeled, any isotype can be used since amelioration of the malignancy in these situations is not dependent upon complement-mediated cytolytic destruction of those cells bearing the SK1 antigen.

The monoclonal antibodies of the invention can be used in any animal in which it is desirable to administer in vitro or in vivo immunodiagnosis or immunotherapy. The term "animal" as used herein is meant to include both humans as well as non-humans.

The term "antibody" as used in this invention is meant to include intact molecules as well as fragments thereof, such as for example, Fab and F(ab')$_2$, which are capable of binding the epitopic determinant.

The invention provides polynucleotides encoding the SK1 antigen. These polynucleotides include DNA, cDNA and RNA sequences which encode SK1. It is understood that all polynucleotides encoding all or a portion of SK1 are also included herein, as long as they encode a polypeptide with SK1 biological activity. Such polynucleotides include naturally occurring, synthetic, and intentionally manipulated polynucleotides. For example, SK1 polynucleotide may be subjected to site-directed mutagenesis. The polynucleotide sequence for SK1 also includes antisense sequences. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of SK1 polypeptide encoded by the nucleotide sequence is functionally unchanged.

Minor modifications of the recombinant SK1 primary amino acid sequence may result in proteins which have substantially equivalent activity and antigenicity as compared to the SK1 polypeptide described herein. Such modifications may be deliberate, as by site-directed mutagenesis, or may be spontaneous. All of the polypeptides produced by these modifications are included herein as long as the biological activity and function of SK1 still exists. Further, deletion of one or more amino acids can also result in a modification of the structure of the resultant molecule without significantly altering its biological activity. This can lead to the development of a smaller active molecule which would have broader utility. For example, one can remove amino or carboxy terminal amino acids which are not required for SK1 biological activity.

The nucleotide sequence encoding the SK1 polypeptide of the invention includes the disclosed sequence and conservative variations thereof. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

DNA sequences of the invention can be obtained by several methods. For example, the DNA can be isolated using hybridization techniques which are well known in the art. These include, but are not limited to: 1) hybridization of genomic or cDNA libraries with probes to detect homologous nucleotide sequences and 2) antibody screening of expression libraries to detect cloned DNA fragments with shared structural features.

Preferably the SK1 polynucleotide of the invention is derived from a mammalian organism, and most preferably from a mouse, rat, or human. Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucl. Acid Res.*, 9:879, 1981).

The development of specific DNA sequences encoding SK1 can also be obtained by: 1) isolation of double-stranded DNA sequences from the genomic DNA; 2) chemical manufacture of a DNA sequence to provide the necessary codons for the polypeptide of interest; and 3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA.

Of the three above-noted methods for developing specific DNA sequences for use in recombinant procedures, the isolation of genomic DNA isolates is the least common. This is especially true when it is desirable to obtain the microbial expression of mammalian polypeptides due to the presence of introns.

The synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al., *Nucl. Acid Res.*, 11:2325, 1983).

A cDNA expression library, such as lambda gt11, can be screened indirectly for SK1 peptides having at least one epitope, using antibodies specific for SK1. Such antibodies can be either polyclonally or monoclonally derived and used to detect expression product indicative of the presence of SK1 cDNA.

DNA sequences encoding SK1 can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the SK1 polynucleotide sequences may be inserted into a recombinant expression vector. The term "recombinant expression vector" refers to a plasmid, virus or other vehicle known in the art that has been manipulated by insertion or incorporation of the SK1 genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., *Gene*, 56:125, 1987), the pMSXND expression vector for expression in mammalian cells (Lee and Nathans, *J. Biol. Chem.*, 263:3521, 1988) and baculovirus-derived vectors for expression in insect cells. The DNA segment can be present in the vector operably linked to regulatory elements, for example, a promoter (e.g., T7, metallothionein I, or polyhedrin promoters).

Polynucleotide sequences encoding SK1 can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

Transformation of a host cell with recombinant DNA may be carried out by conventional techniques as are well known to those skilled in the art. Where the host is prokaryotic, such as *E. Coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the SK1 of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (see for example, *Eukaryotic Viral Vectors*, Cold Spring Harbor Laboratory, Gluzman ed., 1982).

Isolation and purification of microbial expressed polypeptide, or fragments thereof, provided by the invention, may be carried out by conventional means including preparative chromatography and immunological separations involving monoclonal or polyclonal antibodies.

DIAGNOSTIC USES

The monoclonal antibodies of the invention are suited for use, for example, in immunoassays in which they can be utilized in liquid phase or bound to a solid phase carrier. In addition, the monoclonal antibodies in these immunoassays can be detectably labeled in various ways. Examples of types of immunoassays which can utilize monoclonal antibodies of the invention are competitive and non-competitive immunoassays in either a direct or indirect format. Examples of such immunoassays are the radioimmunoassay (RIA) and the sandwich (immunometric) assay. Detection of the antigens using the monoclonal antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The monoclonal antibodies of the invention can be bound to many different carriers and used to detect the presence of SK1. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, and bioluminescent compounds. Those of ordinary skill in the art will know of other suitable labels for binding to the monoclonal antibody, or will be able to ascertain such, using routine experimentation. Furthermore, the binding of these labels to the monoclonal antibody of the invention can be done using standard techniques common to those of ordinary skill in the art.

For purposes of the invention, SK1 may be detected by the monoclonal antibodies of the invention when present in biological fluids and tissues. Any sample containing a detectable amount of SK1 can be used. A sample can be a liquid such as urine, saliva, cerebrospinal fluid, blood, serum and the like, or a solid or semi-solid such as tissues, feces, and the like, or, alternatively, a solid tissue such as those commonly used in histological diagnosis.

Another technique which may also result in greater sensitivity consists of coupling the antibodies to low molecular weight haptens. These haptens can then be specifically detected by means of a second reaction. For example, it is common to use such haptens as biotin, which reacts with avidin, or dinitrophenyl, pyridoxal, and fluorescein, which can react with specific anti-hapten antibodies.

As used in this invention, the term "epitope" is meant to include any determinant capable of specific interaction with the monoclonal antibodies of the invention. Epitopic determinants usually consist of chemically active surface groupings of molecules such as amino acids or sugar side chains and usually have specific three dimensional structural characteristics, as well as specific charge characteristics.

In using the monoclonal antibodies of the invention for the in vivo detection of antigen, the detectably labeled monoclonal antibody is given in a dose which is diagnostically effective. The term "diagnostically effective" means that the amount of detectably labeled monoclonal antibody is administered in sufficient quantity to enable detection of the site having the SK1 antigen for which the monoclonal antibodies are specific.

The concentration of detectably labeled monoclonal antibody which is administered should be sufficient such that the binding to those cells having SK1 is detectable compared to the background. Further, it is desirable that the detectably labeled monoclonal antibody be rapidly cleared from the circulatory system in order to give the best target-to-background signal ratio.

As a rule, the dosage of detectably labeled monoclonal antibody for in vivo diagnosis will vary depending on such factors as age, sex, and extent of disease of the individual. The dosage of monoclonal antibody can vary from about 0.01 mg/m$^2$ to about 500 mg/m$^2$, preferably 0.1 mg/m$^2$ to about 200 mg/m$^2$, most preferably about 0.1 mg/m$^2$ to about 10 mg/m$^2$. Such dosages may vary, for example, depending on whether multiple injections are given, tumor burden, and other factors known to those of skill in the art. For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140–250 keV range, which may be readily detected by conventional gamma cameras.

For in vivo diagnosis radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylenetriaminepentacetic acid (DTPA) and ethylenediaminetetraacetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr, $^{90}$Y, and $^{201}$Tl.

The monoclonal antibodies of the invention can also be labeled with a paramagnetic isotope for purposes of in vivo diagnosis, as in magnetic ,resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and $^{56}$Fe.

The monoclonal antibodies of the invention can be used to monitor the course of amelioration of malignancy in an animal. Thus, by measuring the increase or decrease in the number of cells expressing SK1 or changes in the concentration of SK1 present in various body fluids, it would be possible to determine whether a particular therapeutic regimen aimed at ameliorating the malignancy is effective.

THERAPEUTIC USES

The term "ameliorate" denotes a lessening of the detrimental affect of the malignancy in the animal receiving therapy. The term "therapeutically effective" means that the amount of monoclonal antibody or SK1 used is of sufficient quantity to ameliorate the malignancy.

The term "immunogenically effective amount," as used in the invention, is meant to denote that amount of SK1 antigen which is necessary to induce an ameliorative immune response to the malignancy, for example, by stimulating the production of antibodies which will bind to SK1 epitopes.

SK1 can be administered parenterally by injection, rapid infusion, nasopharyngeal absorption, dermal absorption, and orally. Preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers for occlusive dressings can be used to increase skin permeability and enhance antigen absorption. Liquid dosage forms for oral administration may generally comprise a liposome solution containing the liquid dosage form. Suitable forms for suspending the liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, and sweetening, flavoring, and perfuming agents.

It is also possible for the antigenic preparations containing SK1 to include an adjuvant. Adjuvants are substances that can be used to non-specifically augment a specific immune response. Normally, the adjuvant and the antigen are mixed prior to presentation to the immune system, or presented separately, but into the same site of the animal being immunized. Adjuvants can be loosely divided into several groups based on their composition. These groups include oil adjuvants (for example, Freund's Complete and Incomplete), mineral salts (for example, $AlK(SO_4)_2$, $AlNa(SO_4)_2$, $AlNH_4(SO_4)$, silica, alum, $Al(OH)_3$, $Ca_3(PO_4)_2$, kaolin, and carbon), polynucleotides (for example, poly IC and poly AU acids), and certain natural substances (for example, wax D from *Mycobacterium tuberculosis*, as well as substances found in *Corynebacterium parvum, Bordetella pertussis*, and members of the genus Brucella).

The physical form of the SK1 antigen which is used to immunize an animal can be either aggregated or non-aggregated. Aggregated SK1 can be produced from non-aggregated SK1 by such common techniques as, for example, treatment with glutaraldehyde or other cross-linking agents. The aggregated SK1 thus derived could then be used for purposes of producing a malignancy ameliorating composition effective in inducing an active immune reaction.

However, regardless of whether an animal is immunized with aggregated or non-aggregated, both of these forms of SK1 should cause the production of antibodies to SK1. Thus, it is possible to use these anti-SK1 antibodies diagnostically as, for example, in a kit to detect the presence of SK1 in a specimen.

The SK1 antigen preparations of the invention can be used to induce the production of antibodies which will bind to epitopic determinants of SK1. A particularly useful method in enhancing the production of antibodies to SK1 is to first immunize with the SK1 antigenic preparation of the invention followed by a later immunization.

Many different techniques exist for the timing of the immunizations when a multiple immunization regimen is utilized. It is possible to use the antigenic preparation of the invention more than once to increase the levels and diversity of expression of the immunoglobulin repertoire expressed by the immunized animal. Typically, if multiple immunizations are given, they will be spaced one to two months apart.

Generally, the dosage of SK1 administered to an animal will vary depending on such factors as age, condition, sex and extent of disease, if any, and other variables which can be adjusted by one of ordinary skill in the art.

The antigenic SK1 preparations of the invention can be administered as either single or multiple dosages and can vary from about 50 mg to about 500 mg for the SK1 antigen per dose, more preferably about 50 mg to about 300 mg SK1 antigen per dose, most preferably about 100 mg to about 200 mg SK1 antigen per dose.

The monoclonal antibodies of the invention can also be used, alone or in combination with effector cells (Douillard, et al., *Hybridoma*, 5 (*Supp*. 1: S139, 1986), for immunotherapy in an animal having a tumor which expresses SK1 antigen with epitopes reactive with the monoclonal antibodies of the invention.

When used for immunotherapy, the monoclonal antibodies of the invention may be unlabeled or labeled with a therapeutic agent. These agents can be coupled either directly or indirectly to the monoclonal antibodies of the invention. One example of indirect coupling is by use of a spacer moiety. These spacer moieties, in turn, can be either insoluble or soluble (Diener, et al., *Science*, 231:148, 1986)

and can be selected to enable drug release from the monoclonal antibody molecule at the target site. Examples of therapeutic agents which can be coupled to the monoclonal antibodies of the invention for immunotherapy are drugs, radioisotopes, lectins, and toxins.

The drugs with which can be conjugated to the monoclonal antibodies of the invention include non-proteinaceous as well as proteinaceous drugs. The terms "non-proteinaceous drugs" encompasses compounds which are classically referred to as drugs, for example, mitomycin C, daunorubicin, and vinblastine.

The proteinaceous drugs with which the monoclonal antibodies of the invention can be labeled include immunomodulators and other biological response modifiers. The term "biological response modifiers" is meant to encompass substances which are involved in modifying the immune response in such manner as to enhance the destruction of the antigen bearing tumor for which the monoclonal antibodies of the invention are specific. Examples of immune response modifiers include such compounds as lymphokines. Lymphokines include tumor necrosis factor, interleukins 1, 2, and 3, lymphotoxin, macrophage activating factor, migration inhibition factor, colony stimulating factor, and interferon. Interferons with which the monoclonal antibodies of the invention can be labeled include alpha-interferon, beta-interferon, and gamma-interferon and their subtypes.

In using radioisotopically conjugated monoclonal antibodies of the invention for immunotherapy certain isotypes may be more preferable than others depending on such factors as leukocyte distribution as well as isotype stability and emission. If desired, the tumor cell distribution can be evaluated by the in vivo diagnostic techniques described above. Depending on the malignancy some emitters may be preferable to others. In general, alpha and beta particle-emitting radioisotopes are preferred in immunotherapy. For example, if an animal has solid tumor foci, as in a carcinoma, a high energy beta emitter capable of penetrating several millimeters of tissue, such as $^{90}$Y, may be preferable. On the other hand, if the malignancy consists of simple target cells, as in the case of leukemia, a short range, high energy alpha emitter, such as $^{212}$Bi, may be preferable. Examples of radioisotopes which can be bound to the monoclonal antibodies of the invention for therapeutic purposes are $^{125}$I, $^{131}$I, $^{90}$Y, $^{67}$Cu, $^{212}$Bi, $^{211}$At, $^{212}$Pd, $^{47}$Sc, $^{109}$Pd, and $^{188}$Re.

Lectins are proteins, usually isolated from plant material, which bind to specific sugar moieties. Many lectins are also able to agglutinate cells and stimulate lymphocytes. However, ricin is a toxic lectin which has been used immunotherapeutically. This is preferably accomplished by binding the alpha-peptide chain of ricin, which is responsible for toxicity, to the antibody molecule to enable sit e specific delivery of the toxic effect.

Toxins are poisonous substances produced by plants, animals, or microorganisms that, in sufficient dose, are often lethal. Diphtheria toxin is a substance produced by *Corynebacterium diphtheria* which can be used therapeutically. This toxin consists of an alpha and beta subunit which under proper conditions can be separated. The toxic A component can be bound to an antibody and used for site specific delivery to a SK1 bearing cell for which the monoclonal antibodies of the invention are specific. Other therapeutic agents which can be coupled to the monoclonal antibodies of the invention are known, or can be easily ascertained, by those of ordinary skill in the art.

The labeled or unlabeled monoclonal antibodies of the invention can also be used in combination with therapeutic agents such as those described above. Especially preferred are therapeutic combinations comprising the monoclonal antibody of the invention and immunomodulators and other biological response modifiers.

Thus, for example, the monoclonal antibodies of the invention can be used in combination with alpha-interferon. This treatment modality enhances monoclonal antibody targeting of carcinomas by increasing the expression of monoclonal antibody reactive antigen by the carcinoma cells (Greiner, et al., *Science*, 235:895, 1987). Alternatively, the monoclonal antibody of the invention could be used, for example, in combination with gamma-interferon to thereby activate and increase the expression of Fc receptors by effector cells which, in turn, results in an enhanced binding of the monoclonal antibody to the effector cell and killing of target tumor cells. Those of skill in the art will be able to select from the various biological response modifiers to create a desired effector function which enhances the efficacy of the monoclonal antibody of the invention.

When the monoclonal antibody of the invention is used in combination with various therapeutic agents, such as those described herein, the administration of the monoclonal antibody and the therapeutic agent usually occurs substantially contemporaneously. The term "substantially contemporaneously" means that the monoclonal antibody and the therapeutic agent are administered reasonably close together with respect to time. Usually, it is preferred to administer the therapeutic agent before the monoclonal antibody. For example, the therapeutic agent can be administered 1 to 6 days before the monoclonal antibody. The administration of the therapeutic agent can be daily, or at any other interval, depending upon such factors, for example, as the nature of the tumor, the condition of the patient and half-life of the agent.

Using the monoclonal antibodies of the invention, it is possible to design therapies combining all of the characteristics described herein. For example, in a given situation it may be desirable to administer a therapeutic agent, or agents, prior to the administration of the monoclonal antibodies of the invention in combination with effector cells and the same, or different, therapeutic agent or agents. For example, it may be desirable to treat patients with malignant disease by first administering gamma-interferon and interleukin-2 daily for 3 to 5 days, and on day 5 administer the monoclonal antibody of the invention in combination with effector cells as well as gamma-interferon, and interleukin-2.

It is also possible to utilize liposomes with the monoclonal antibodies of the invention in their membrane to specifically deliver the liposome to the area of the tumor expressing SK1. These liposomes can be produced such that they contain, in addition to the monoclonal antibody, such immunotherapeutic agents as those described above which would then be released at the tumor site (Wolff, et al., *Biochemical et Biophysical Acta*, 802:259, 1984).

The dosage ranges for the administration of the monoclonal antibodies of the invention are those large enough to produce the desired effect in which the symptoms of the malignant disease are ameliorated. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any complication. Dosage can vary from about 0.1 mg/kg to about 2000 mg/kg, preferably about 0.1 mg/kg to about 500 mg/kg, in one or more dose administrations daily, for one or several days. Generally, when the monoclonal antibodies of the invention are administered conjugated with therapeutic agents lower dosages, comparable to those used for in vivo immunodiagnostic imaging, can be used.

The monoclonal antibodies of the invention can be administered parenterally by injection or by gradual perfusion over time. The monoclonal antibodies of the invention can be administered intravenously, intraperitoneally, intramuscularly, subcutaneously, intracavity, or transdermally, alone or in combination with effector cells.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The invention also relates to a method for preparing a medicament or pharmaceutical composition comprising the SK1 antigen, or the monoclonal antibodies of the invention, the medicament being used for therapy of malignant disorders.

The above disclosure generally describes the present invention. A more complete understanding can be obtained by reference to the following specific examples which are provided for purposes of illustration only, and are not intended to limit the scope of the invention.

EXAMPLE 1

PREPARATION OF HYBRIDOMA CELL LINES PRODUCING MONOCLONAL ANTIBODY TO SK1

Lymphocytes isolated from a lymph node of a 60 year-old male with Duke's 'B' colon carcinoma were used to generate hybridoma cell lines producing monoclonal antibody to SK1. Lymphocytes were cultured in complete medium with either 25% supernatant of pokeweed mitogen-stimulated T lymphocytes (sPWM-T) or 25% supernatant of mixed lymphocyte culture (sMLC) (vol/vol). Carcinoembryonic antigen (CEA) was used for in vitro immunization (IVI). Purified CEA at various concentrations was added to the stimulated lymphocytes for a period of 5 to 6 days. At the end of the culture, the viability of the lymphocytes was determined by 0.05% trypan blue exclusion prior to fusion with human cell line SHFP-1. The mean viability was approximately 70%.

Briefly, sPWM-T was prepared by first obtaining peripheral blood lymphocytes by FICOLL-HYPAQUE™ density gradient centrifugation (Pharmacia, Piscataway, N.J.). The lymphocytes were then treated with L-leucine methyl ester, 2.5 mmol/L (Sigma, St. Louis, Mo.), to reduce inhibitory cells (natural killer-like cells, cytotoxic T lymphocytes, and a subset of $CD8^+$ T cells) for IVI, as described previously (Thiele, et al., *J. Immunol.*, 134:786, 1985). The T helper-enriched preparation was obtained by incubating the L-leucine methyl ester-treated lymphocytes with sheep red blood cells (Cappel, Durham, N.C.). The sheep red blood cells were then lysed with red blood cell lysing solution (Sigma). A 1:100 dilution of pokeweed mitogen (GIBCO, Grand Island, N.Y.) was added to T cells at a concentration of $4 \times 10^9$/L in complete RPMI 1640 supplemented with 10% autologous serum and incubated for 48 hours. The supernatant obtained after centrifugation to remove the pokeweed mitogen-stimulated T cells was designated sPWM-T. Supernatant of mixed lymphocyte culture (sMLC) was prepared by mixing heterologous lymphocytes of two patients at a ratio of 1:1, with a final concentration of $4 \times 10^9$/L, and cultured for 72 hours. Both supernatants were stored at $-20°$ C. until used.

A human B lymphoblastoid cell line derived from parental WIL-2 cells (Glassy, *J. Tissue Culture Methods*, 12:85, 1989), SHFP-1, was the human fusion partner cell line. Colon cancer cell lines HT-29 and Caco2 were obtained from American Type Culture Collection, Rockville, Md. These cell lines were cultured in RPMI 1640 medium supplemented with 10% to 20% fetal calf serum.

In the fusion procedure, one part of lymphocytes from the lymph nodes and two parts of SHFP-1 cells were fused with 50% polyethylene glycol 1500 (Behringer Mannheim, Germany). The hybrids were selected by medium containing hypoxanthine, aminopterin, and thymidine (Behringer Mannheim). Reactivity to HT-29 cells, reactivity to carcinoembryonic antigen, and isotype of immunoglobulin by enzyme-linked immunosorbent assay (ELISA) were determined for the supernatant of each visible hybridoma. The reactive clones were subcloned by limiting dilution (Glassy, et a., *Cancer Invest.*, 5:449, 1987).

Immunoglobulin production and tumor reactivity were evaluated by enzyme-linked immunosorbent assay (ELISA). The ELISA plates were prepared by coating the plates with HT-29 or Caco2 cells at $5 \times 10^4$ cells per well. After blocking with phosphate-buffered saline-0.5% bovine serum albumin solution, 50 μL of the testing supernatant was added to each well for 1 to 2 hours at room temperature. After washing, horseradish peroxidase-conjugated goat anti-human immunoglobulin (anti-IgM and anti-IgG were from Jackson, West Grove, Pa., and anti-IgA was from Zymed, San Francisco, Calif.) was added for an incubation of 45 minutes. The substrate, orthophenylenediamine, was added for color reaction. The plates were read at 492 nm with a microplate reader (MR 700, Dynatech Laboratories, Inc., Chantilly, Va.). The background optical density ($OD_b$) was obtained by substituting phosphate-buffered saline-bovine serum albumin solution for the testing supernatant and was found to be 0.050 or lower. At the 96-well stage, supernatants with ODs greater than 0.250 were regarded as positive. Subsequently, because few IgM-secreting clones bound nonspecifically to the ELISA plates, new criteria were established to evaluate the ELISA results:

Criterion A:$\Delta OD<1.000$ and $OD_s-OD_f>0.200$, and

Criterion B:$\Delta OD\geq 1.000$ and $OD_s-OD_f>0.150$, where $\Delta OD=OD_s-OD_b$, $OD_s$ (sample OD) represents the OD obtained from specific binding of supernatant to the antigen-coated ELISA plates, and $OD_f$ (false OD) represents the OD obtained from nonspecific binding of supernatant to the ELISA plates without antigen coating.

EXAMPLE 2

IMMUNOLOGICAL REACTIVITY OF HuMAb (SK1)

Various human carcinoma cell lines were tested for their reactivity with HuMAb(SK1). Cell lines tested were HT29, Caco2, COL205, COL320DM, Panc-1, KATO III, Calu-1, A375, and HTB63 (ATCC, Rockville, Md.) and P3 and M21 (UCLA).

All the cells were maintained in RPMI 1640 medium (Whittaker, Wallsville, Md.) supplemented with 10–20% FCS (Hyclone Lab., Logan, Utah) and 2 mM L-glutamine (Whittaker) except HT29 cells which were grown in McCoy's 5A (UCSD Core Facility, La Jolla, Calif.); Panc-1 and Calu-1 cells were grown in DME-high glucose medium (UCSD Core Facility, La Jolla, Calif.). Twenty ml of cell suspension at $5\times10^4$/ml were added to each petri dish containing a sterile glass slide. After various periods of culture, the slides were harvested and used for either immunoperoxidase (IP) or immunofluorescence (IF) staining.

In preparing the slides for staining, the slides with seeded cells were washed in PBS and fixed with cold acetone. For indirect IP staining, fixed cells were incubated with the HuMAb (SK1) supernatant (10 μg/ml) and subsequently developed with horseradish peroxidase-conjugated goat anti-human IgM, followed by diaminobenzidine (DAB; Sigma) containing 0.01% $H_2O_2$. After counterstaining with Mayer's hematoxylin, the specimens were cleared with ammonium peroxide and mounted with aqua-mount. In IF stainings, a 1:200 dilution of FITC conjugated goat antibody to human IgM (Boehringer Mannheim) was used as second antibody and reactivities were evaluated by Nikon fluorescence microscopy. Controls consisted of secondary antibody and cells.

In HT29 cells (colon cancer), one day old cultures and peripheral tumor cells of 3 day old colonies were stained intensely. This was in contrast to the infrequent staining observed in the centers of the colonies. When cells were confluent on the fifth day, the staining of SK1 was uniformly diminished. The decreased antigen expression as a function of time was also observed in cultured Calu-1 cells (lung cancer). The antigen was evenly detected in the cytoplasm at the beginning of the culture (Day 1); subsequently, it concentrated at one end of the nucleus and the nuclei were often dented toward the antigen concentrated areas. On Days 4 and 5, the antigen became diffuse and the reactivities were weakened and eventually disappeared by day 7. A similar immunocytochemical finding was seen with Panc-1 cells (pancreatic cancer). This data suggests that the expression of SK1 is proliferation related.

EXAMPLE 3

FLOW CYTOMETRY

HT29 cells were examined by flow cytometry to determine membrane and cytoplasmic staining of SK1 using HuMAb(SK1). The HT29 cells were harvested from 1 day, 2 day, and 5 day old tissue cultures by 0.2% ethylenediamine tetra-acetic acid (EDTA) in $Ca^{2+}$ and $Mg^{2+}$ free PBS. Cells were washed with PBA (PBS with 1% albumin). For cytoplasmic staining, cells were fixed with 0.5% paraformaldehyde for 30 min and subsequently incubated with supernatant containing HuMAb(SK1) (10 to 25 μg/ml) for 1 h. After washing, a 1:500 dilution of FITC-conjugated goat anti-human IgM (Boehringer Mannheim Biochemicals, Indianapolis, Ind.) was added for 1 h. All steps were performed at 4° C. Five to twenty thousand cells were examined using an ORTHO CYTOFLUOROGRAF™ 50-H with argon laser for FITC and PI (488 nm), interfaced with a Data General 2150 Computer. The autofluorescence of unstained cells and second antibody control were included. The non-fixed viable cells were used for membrane reactivity and were fixed with 1% formalin upon the completion of staining. DNA was stained with propidium iodide (PI, Sigma) at 50 μg/ml for 30 min in 10 mM Tris, pH 7.0, with 5 mM $MgCl_2$.

Flow cytometric studies showed that antigen SK1 was both on the cell surface and in the cytoplasm. A decrease of SK1 positive cells as a function of in vitro culturing time was observed by both surface and intracellular staining with HuMAb(SK1) (Table 1).

TABLE 1

PROGRESSIVE LOSS OF AgSK1 IN NONPROLIFERATING CELLS

| | % AgSK1 POSITIVE CELLS | | | | | |
|---|---|---|---|---|---|---|
| | Day 1 | | Day 2 | | Day 5 | |
| Cell Line | Cytoplasmic | Surface | Cytoplasmic | Surface | Cytoplasmic | Surface |
| HT29 | 89 | 44 | 66 | 6 | 47 | 0 |
| Panc1 | 81 | 71 | 65 | 51 | 46 | 0 |

In conjunction with DNA analysis of proliferating HT29, the SK1 was detected throughout the cell cycle (from G1 to M) suggesting that SK1 was being synthesized at early G1 phase and persisted thereafter.

The reactivity of HuMAb(SK1) was also tested on histological specimens derived from various tumor tissues.

TABLE 2

REACTIVITY OF HuMAb(SK1) WITH VARIOUS TUMOR TISSUES

| TUMOR TISSUE | REACTIVITY[1] |
|---|---|
| colorectal | 10/10 |
| gastric | 1/1 |
| pancreatic | 1/1 |
| lung (adenocarcinoma) | 2/2 |
| breast | 0/2 |
| melanoma | 0/4 |
| sarcoma (soft tissue) | 0/4 |

[1]expressed as (# positive/# tested)

As shown in Table 2, HuMAb(SK1) was highly reactive with tumors of the gut, pancreas, and lung, but did not react with specimens of breast, melanoma, and soft tissue sarcoma.

EXAMPLE 4

CHARACTERIZATION OF SK1

The effect of various agents on antigen SK1 was evaluated using ELISA plates coated with HT29 cells. The ELISA plates were treated with various agents under the following conditions: 0.45 U/ml neuraminidase (Type III, Sigma) pH 5.5, 37° C., overnight; periodic acid (Sigma) 5 mM in sodium acetate buffer, pH 4.5, for 45 min at RT; 0.25% trypsin (Gibco, Grand Island, N.Y.), pH 7.8, 37° C. for 20 min; and heat treatment at 100° C. for 2 min. In determining the sensitivity of SK1 to NP-40, SK1 positive cells were mixed with NP-40 and then centrifuged. SK1 reactivity was then tested on the harvested supernatant using ELISA. The sensitivity of SK1 to trypsin and heat was further analyzed by SDS-PAGE and Western blot. As summarized in Table 3, treating target cells with neuraminidase, trypsin, periodate, and heat abolished the binding with HuMAb(SK1) suggesting a sialoglycoprotein nature of SK1.

TABLE 3

SENSITIVITY OF AgSK1 TO VARIOUS AGENTS

| | AGENT | | | | |
|---|---|---|---|---|---|
| | Neuraminidase | Heat | Trypsin | Periodic Acid | NP-40 | Untreated |
| Reaction[1] | — | — | — | — | + | + |

[1]Reactivity with HuMAb(SK1) after treatment

SK1 was also evaluated using lysates of various cell lines. In preparing the lysates, HT29, Panc-1, KATO III and Calu-1 cells were washed 3 times in Tris-buffered saline (TBS) and resuspended with TBS at $5 \times 10^7$ cells/ml. The cell lysates were prepared by repeated freezing and thawing (4x) and centrifugation at 3000xg for 10 min. The supernatants were collected and stored at −70° C. until use. The cell lysates were then tested by SDS-PAGE and Western Blot. Electrophoresis was performed using the Novex X-cell mini-gel system (Novex, San Diego, Calif.). Precast 8–16% Tris-glycine gels (Novex) were used to run all samples. Following electrophoresis, proteins were transferred onto nitrocellulose membranes using the Bio-Rad transfer system (Richmond, Calif.). Protein standards and prestained standards (Sigma) were used simultaneously. After blocking with TBA (TBS—1% albumin) the membranes were washed, dried, and incubated in hybridoma-supernatants at 25 µg/ml. Alkaline phosphatase conjugated goat anti-human IgM (American, Qualex, La Marada, Calif.) at a dilution of 1:3000 was used as the secondary antibody. The bands were developed using the Proto Blot System from Promega.

These studies showed that SK1 is a two chain structure with molecular weights estimated to be 42–46 kDa by gel electrophoresis and Western blot under both reducing and non-reducing conditions. The antigen was identified in cell lysates of 1 to 2 day old cultures of the following cells: HT29, Panc-1, KATO III. The antigen was marginally detectable when the 5 day cultures were used. In contrast to the above carcinoma cells, the melanoma cell lines HTB63, HTB66, HTB71, HTB72, HTB73, UCLA M21, and UCLA M14 had no detectable antigen SK1 by both gel electrophoresis with Western blot and cytoimmunoperoxidase staining.

EXAMPLE 5

BIOLOGICAL ACTIVITY OF ANTIGEN SK1

The following experiments provide both in vitro and in vivo data which support the use of monoclonal antibody SK1 in the treatment of animals, including humans.

The Examples above and the following experiments show in in vitro studies demonstrating the specific reactivity of SK-1 monoclonal antibody of the invention with colon cancer cells. The results are shown in an SK1-monoclonal antibody-mediated complement-dependent cellular cytotoxicity (CDCC) assay against carcinoma cell lines and fresh colon carcinoma cells. Use of the CDCC assay is one of the primary methods currently in use to evaluate an antibody's ability to lyse target cells.

AgSK1 positive cells, such as the KATO-III cell line were used as targets. An antibody capable of fixing complement (a family of proteins in serum which are capable of causing the lysis/death of certain cell types) was incubated with the target cells and then complement. The target antigen positive cells were loaded with 51-Cr and the release of the radioactive CPM is directly proportional to the number of cells lysed.

Approximately 2–5×10⁶ cells were incubated with 200 uCi of 51-Cr, in a total volume of not more than 0.5 ml, at 37° C. for 1 hr, then at room temperature for 15–20 min to allow for the release of "loosely bound" 51-Cr. The cells were then counted, adjusted to a concentration of 5000 cpm/50 ul/well, and 50 ul added to each well of a 96-well plate. Upon completion, the appropriate concentration of the test monoclonal antibody was added to each well and incubated for 60 min. The plates are centrifuged (150×g for 5 min), "flicked" off supernatant, then 100 ul of fresh media was added to each well, then the wash step was repeated. After flicking off the final wash solution, 50 ul of the test complement (Pel-Freeze; HLA-ABC absorbed) at the appropriate dilution was added to the wells for a 45 min incubation at 37° C. Then, 50 ul of fresh media was added to each well and centrifuged as before. Following the centrifugation, 50 ul of supernatant was removed from each well and counted in a gamma counter. Table 4 shows that, as described in the present patent application, the SK1 monoclonal antibody selectively and effectively lysed colon cancer cells (HT29), pancreatic cancer cells (Panc-1) and cancer cells derived from surgical specimens (Colon cancer cells pt.#1 and #2) in the CDCC assay.

In contrast, antibody (10 ug/ml) and complement alone showed no detectable cytotoxicity, and normal colonic mucosal cells bearing no detectable antigen was resistant to SK1 in the CDCC assay (Table 4). Specific cytotoxicity was shown to be dose dependent. CDCC was most remarkable at the highest testing dose, i.e., 10 ug/ml. The specific cytotoxicity of SK1 against colon cancer cells in patient #1 (pt #1) was detectable at a serial dilution of antibody up to 1:16.

TABLE 4

SK1 MEDIATED CDCC AGAINST CARCINOMA CELL LINES AND FRESH COLON CARCINOMA CELLS

| CELLS | CDCC % |
|---|---|
| HT29 | 100 |
| Panc-1 | 83 |
| Colon Cancer (Pt. #1) | 81 |
| Normal colon mucosal cells (Pt. #1) | 15 |
| Colon cancer cells (Pt. #2) | 60 |

The concentration of SK1 was tested at 10 μg/ml.
Background release was 6%.

An additional in vitro CDCC assay was performed as described above using Kato-III, Panc-1, or primary colon cells. The results are shown in Table 5. The results of the assay show between 65% and 100% lysis of SK1⁺ cells by SK1 antibody.

TABLE 5

CDCC ANALYSIS

| Expt | AgSK1⁺ Cell Line | % Release | % Surface[1] AgSK1⁺ | % Killing AgSK1⁺ Cells |
|---|---|---|---|---|
| 1 | Kato-III | 25.6% | 23.2% | 90% |
| 2 | Kato-III | 6.0% | 4.0% | 65% |
| 3 | Panc-1 | 18.0% | 21.0% | 100% |
| 4 | Kato-III | 25.7% | 28.3% | 100% |
| 5 | Kato-III | 4.3% | 6.6% | 100% |
| 6 | Primary colon | 20.0% | N.D. | N.D. |

[1]As determined by FACS analysis.

In addition, in vivo data showing the pharmacological effects of SK1 in a nude mouse model, is described in Table 6 and FIG. 1. Briefly, Panc-1, pancreatic cancer cells (5×10⁶ cells/mouse), were injected into three groups of nude mice (Balb/c, Harlan, Sprague-Dawley) on day 0. Immediately after tumor implantation, one group of mice was injected intraperitoneally (IP) with PBS (500 ul/mouse), one group with polyclonal human IgM (300 ug/mouse in 500 ul), and one group was injected with the SK1 monoclonal antibody of the invention (300 ug/mouse in 500 ul). Tumor size was measured every week for 4 weeks.

The tumor size was significantly suppressed in all of the mice in the group treated with the SK1 monoclonal antibody, as shown in FIG. 1 and Table 6. The animal model used for these studies is a well accepted model which is considered to be predictive of results in humans.

TABLE 6

SK1 NUDE MOUSE XENOGRAFT MODEL

| SAMPLE[a] | WEEK | | | |
|---|---|---|---|---|
| | 1 | 2 | 3 | 4 |
| PBS ● | 128 ± 41[d] | 726 ± 251 | 6820 ± 687 | 16210 ± 2353 |
| IgM[b] ■ | 104 ± 56 | 693 ± 275 | 7273 ± 1297 | 16938 ± 2387 |
| SK1[c] ▲ | 68 ± 40 | 148 ± 69 | 677 ± 259 | 3118 ± 1016 |

[a]Sample injection volumes of PBS, IgM and SK1 were all at 500 ul/mouse. Each group consisted of 7 mice, for a total of 21 mice.
[b]Control polyclonal IgM (Sigma) injected (300 ug) immediately after implantation of the Panc-1 tumor cells (5 × 10⁶ cells per mouse).
[c]SK1 derived from tissue culture supernatant was injected (300 ug) immediately after implantation of the Panc-1 tumor cells (5 × 10⁶ cells per mouse).
[d]Tumor size = $\frac{(\text{length} \times \text{width})^2}{2}$; 7 mice = x ± y

EXAMPLE 6

CHARACTERIZATION OF AGSK1

Previous studies have identified several forms of AgSK1 in human colon tumors and in the colon adenocarcinoma cell line HT29 (Chang, et al. *Cancer Research*, 53: 1122–1127, 1993). These forms include a doublet migrating at about 42–46 kDa on SDS-PAGE. Our analysis showed the expression of the 42–46 kDa doublet in various human carcinoma cell lines using Western blot analysis with the antibody of the invention.

Cells were harvested at 50% confluency (or 90% as indicated). Whole cells were pelleted, washed in PBS, repelleted and lysed in a hypotonic solution containing 1.0%

NP40. The nuclei were separated from cytosolic proteins via a brief spin at high speed in a microfuge. The nuclei were lysed in 10% glycerol/Tris pH 6.8 and DNA sheared by repeated passage through a 25 gauge needle to reduce viscosity. The protein concentration of each fraction was determined by BCA assay (Pierce) and 40 ug of each were loaded on a 8–16% mini PAGE gel (Novex) after mixing 1:1 with 2× non-reducing sample loading buffer (Novex). The proteins were blotted electrophoretically using a modified method of Towbin (*Proc. Nat. Acad. Sci.*, 76: 5\4350–4354, 1979) in a Novex apparatus. The blot was processed using the procedure described above for plaque lift screening.

Figure 2:
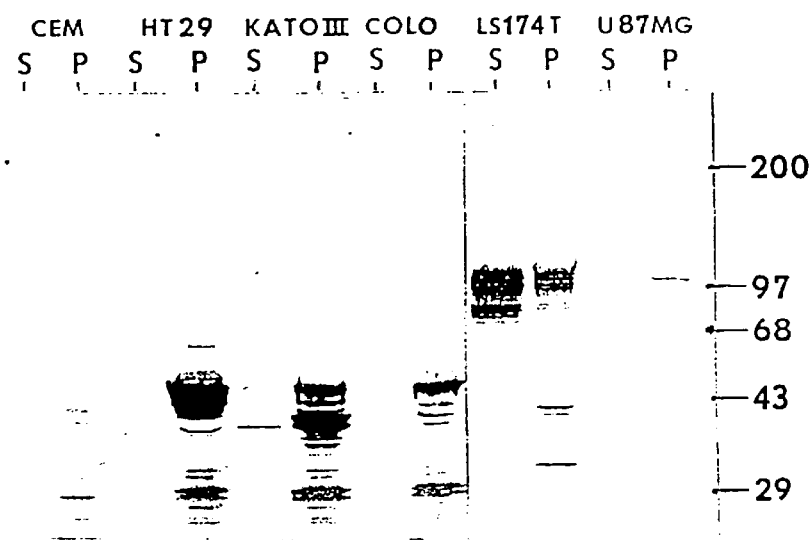
FIG. 2 is an SDS-PAGE gel showing the 42–46kD SK1 antigen in human cell lines (S=supernatant; P=nuclear pellet).

FIG. 2 shows that the doublet was detected in the nuclear pellets of HT29, KatoIII and Colo205 cells. The glioma line, U87MG, and T-cell line, CEM, were negative for the antigen.

EXAMPLE 7

REACTIVITY OF HuMAb-SK1 WITH VARIOUS TUMOR TISSUES

Additional tissues were stained using the immunochemical methods as described in Example 2. The results in Table 6 show the high reactivity of monoclonal antibody SK1 (MAbSK1) with colorectal cancer cells.

TABLE 6

IMMUNOCHEMICAL STAINING
OF HUMAN TISSUES WITH HuMAb-SK1

| Tissues | # Tissues AgSK1 + | # Tissues AgSK1 trace | # Tissues AgSK1 – |
|---|---|---|---|
| Colorectal Cancer | 24 | 0 | 0 |
| Colorectal mucosa | 1 | 0 | 1 |
| Small intestine mucosa | 0 | 0 | 2 |
| Stomach cancer | 1 | 0 | 0 |
| Stomach mucosa | 0 | 0 | 2 |
| Pancreatic cancer | 2 | 0 | 0 |
| Pancreas | 0 | 2 | 3 |
| Liver | 0 | 2 | 3 |
| Lung cancer | 2 | 0 | 0 |
| Lung | 0 | 0 | 4 |
| Skin squamous cell cancer | 1 | 0 | 0 |
| Kidney | 0 | 1 | 4 |
| Brain | 0 | 0 | 4 |
| Melanoma | 0 | 0 | 4 |
| Sarcoma | 0 | 0 | 4 |
| Breast cancer | 0 | 0 | 3 |
| Prostate | 0 | 0 | 3 |
| Skin | 0 | 0 | 3 |
| Esophagus | 0 | 0 | 3 |
| Stomach | 0 | 0 | 3 |

| Tissues | # Tissues AgSK1 + | # Tissues AgSK1 trace | # Tissues AgSK1 |
|---|---|---|---|
| Bladder | 0 | 0 | 3 |
| Testis | 0 | 0 | 3 |
| Ovary | 0 | 0 | 3 |
| Uterus | 0 | 0 | 3 |
| Spleen | 0 | 0 | 3 |
| Thyroid | 0 | 0 | 3 |
| Heart | 0 | 0 | 3 |
| Bone Marrow | 0 | 0 | 3 |
| Eye | 0 | 0 | 3 |
| Nerve | 0 | 0 | 4 |
| Skeletal Muscle | 0 | 0 | 3 |
| Salivary Gland | 0 | 0 | 1 |

DEPOSIT OF MATERIALS

The following cell line has been deposited with the American Type Culture Collection, 1301 Parklawn Drive, Rockville, Md., USA (ATCC) on Oct. 24, 1991:

| Cell Line | ATCC Accession No. |
|---|---|
| SK1 | HB 10905 |

The deposit was made under the provisions of the Budapest Treaty on the International Recognition of the Deposit of Microorganisms for the Purpose of Patent Procedure and the Regulations thereunder (Budapest Treaty). This assures maintenance of viable cultures for 30 years from the date of deposit. The organisms will be made available by ATCC under the terms of the Budapest Treaty which assures permanent and unrestricted availability of the progeny of the culture to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

If the culture deposit should die or be lost or destroyed when cultivated under suitable conditions, it will be promptly replaced on notification with a viable specimen of the same culture. Availability of a deposited strain is not to be construed as a license to practice the invention in contravention of the rights granted under the authority of any government in accordance with its patent laws.

The invention now being fully described, it will be apparent to one of ordinary skill in the art that many changes and modifications can be made without departing from the spirit or scope of the invention.

What is claimed is:

1. A method of detecting SK1 which comprises contacting a source suspected of containing SK1 with a diagnostically effective amount of detectable labeled antibody or fragment thereof, having the specificity of the antibody produced by hybridoma cell line ATCC HB 10905 and determining whether the antibody binds to the source.

2. A method of detecting SK1 which comprises contacting a source suspected of containing SK1 with a diagnostically effective amount of detectable labeled antibody or fragment thereof, wherein the antibody is produced by hybridoma cell line ATCC HB 10905 and determining whether the antibody binds to the source.

3. The method of claim 1, wherein the detecting is in vivo.

4. The method of claim 3, wherein the detectable label is selected from the group consisting of a radioisotope and a paramagnetic label.

5. The method of claim 1, wherein the detecting is in vitro.

6. The method of claim 5, wherein the detectable label is selected from the group consisting of a radioisotope, a fluorescent compound, a colloidal metal, a chemiluminescent compound, a bioluminescent compound and an enzyme.

* * * * *